United States Patent
Maruyama et al.

(10) Patent No.: US 8,380,037 B2
(45) Date of Patent: Feb. 19, 2013

(54) LATERAL LIGHT EMITTING DEVICE AND METHOD OF PRODUCING THE SAME

(75) Inventors: Naofumi Maruyama, Kanagawa (JP); Toshiaki Fukuda, Kanagawa (JP)

(73) Assignee: Toyo Glass Co., Ltd., Tokyo (JP)

( * ) Notice: Subject to any disclaimer, the term of this patent is extended or adjusted under 35 U.S.C. 154(b) by 0 days.

(21) Appl. No.: 13/142,933

(22) PCT Filed: Mar. 3, 2010

(86) PCT No.: PCT/JP2010/053402
§ 371 (c)(1),
(2), (4) Date: Jun. 30, 2011

(87) PCT Pub. No.: WO2011/108087
PCT Pub. Date: Sep. 9, 2011

(65) Prior Publication Data
US 2011/0316029 A1     Dec. 29, 2011

(51) Int. Cl.
*G02B 6/10* (2006.01)
(52) U.S. Cl. .................................................. 385/146
(58) Field of Classification Search .................. None
See application file for complete search history.

(56) References Cited

U.S. PATENT DOCUMENTS

| | | | | |
|---|---|---|---|---|
| 5,320,620 A * | 6/1994 | Long et al. | | 606/28 |
| 5,428,699 A * | 6/1995 | Pon | | 385/31 |
| 5,772,658 A * | 6/1998 | Konwitz | | 606/15 |
| 6,445,939 B1 * | 9/2002 | Swanson et al. | | 600/342 |
| 6,453,090 B1 | 9/2002 | Conde et al. | | |
| 7,909,817 B2 * | 3/2011 | Griffin et al. | | 606/13 |
| 2002/0118908 A1 | 8/2002 | Conde et al. | | |
| 2004/0247268 A1 | 12/2004 | Ishihara et al. | | |
| 2005/0185901 A1 | 8/2005 | Inoue et al. | | |
| 2007/0232902 A1 | 10/2007 | Teramura | | |
| 2008/0002529 A1 | 1/2008 | Sekine et al. | | |
| 2009/0190883 A1 | 7/2009 | Kato et al. | | |
| 2009/0262361 A1 | 10/2009 | Tanioka et al. | | |
| 2012/0069861 A1 * | 3/2012 | Neuberger | | 372/6 |

FOREIGN PATENT DOCUMENTS

| | | |
|---|---|---|
| JP | 2-77001 | 3/1990 |
| JP | 3-279908 | 12/1991 |
| JP | 6-35946 | 5/1994 |

(Continued)

OTHER PUBLICATIONS

International Search Report issued Apr. 6, 2010 in International (PCT) Application No. PCT/JP2010/053402, together with English translation thereof.

(Continued)

*Primary Examiner* — Sung Pak
(74) *Attorney, Agent, or Firm* — Wenderoth Lind & Ponack, L.L.P.

(57) ABSTRACT

A lateral light emitting device is formed by fusing one end of a rod lens to an end surface of an optical fiber, and by fusing a prism to another end of the rod lens. The prism has a basic shape including a planar light emitting surface parallel to an axis formed by cutting part of a circumference of a cylinder and has a distal end inclined surface, a distal end portion of which is diagonally cut. Alternatively, a prism lens is fused to the end surface of the optical fiber. The prism lens has the same basic shape described above.

10 Claims, 18 Drawing Sheets

FOREIGN PATENT DOCUMENTS

| | | |
|---|---|---|
| JP | 11-56786 | 3/1999 |
| JP | 2000-509853 | 8/2000 |
| JP | 2004-317437 | 11/2004 |
| JP | 2005-241822 | 9/2005 |
| JP | 2007-275193 | 10/2007 |
| JP | 2008-200283 | 9/2008 |
| WO | 01/11409 | 2/2001 |
| WO | 2007/099947 | 9/2007 |
| WO | 2008/081653 | 7/2008 |

OTHER PUBLICATIONS

Japanese Office Action dated Aug. 31, 2010 in corresponding Japanese Patent Application No. 2010-519301, together with English translation thereof.

Supplementary European Search Report issued Jul. 23, 2012 in European Patent Application No. EP 10 84 6992.

* cited by examiner

Fig. 7
(a) 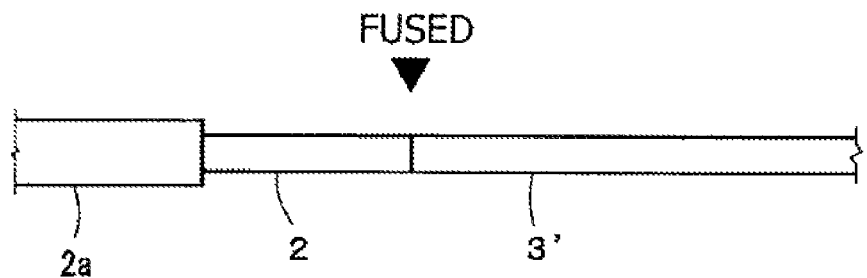
(b) 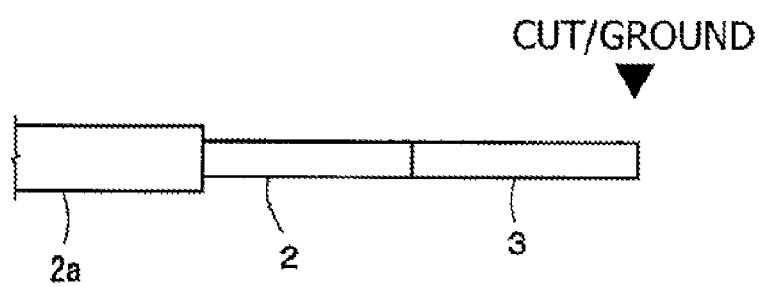
(c) 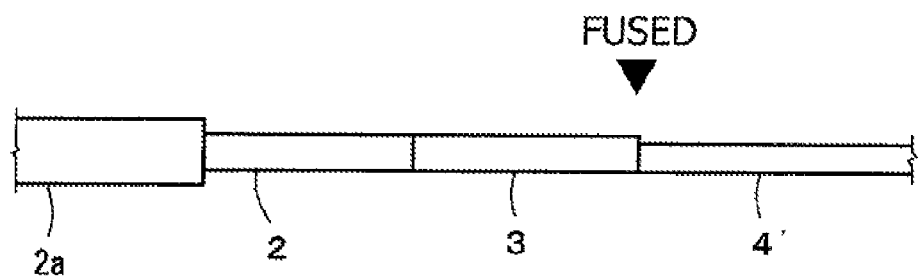
(d) 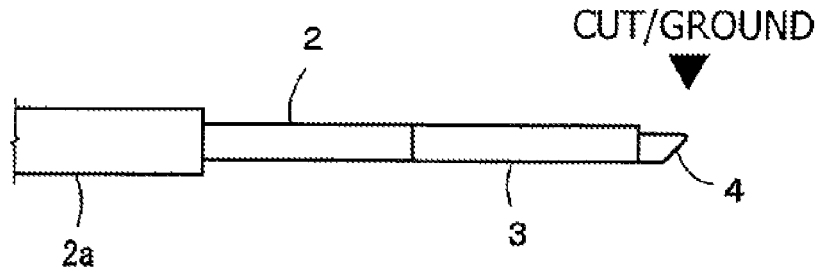

Fig. 9
(a) 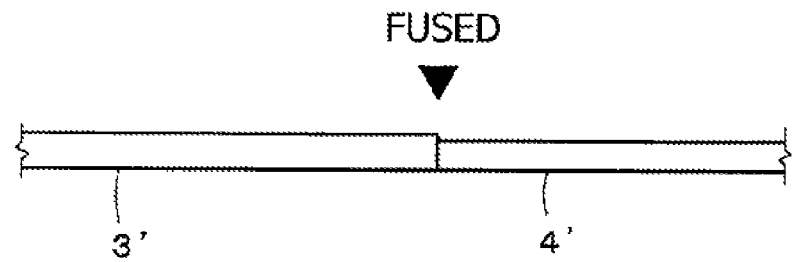
(b) 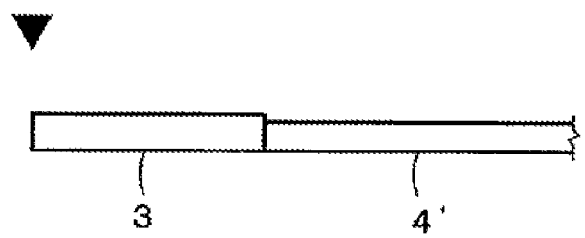
(c) 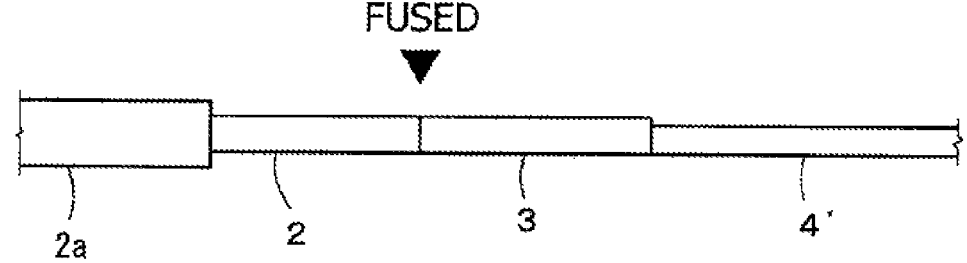
(d) 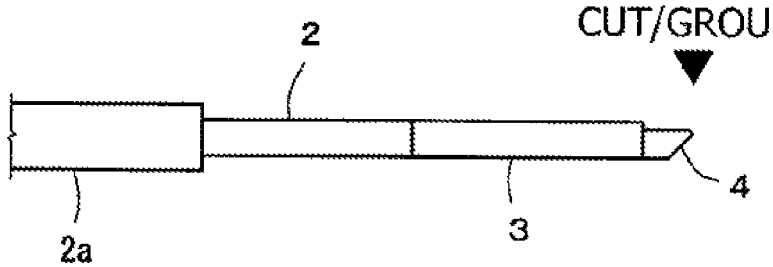

Fig. 11
(a) 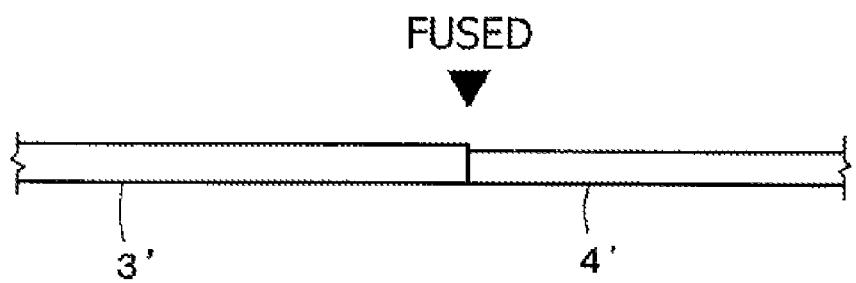
(b) 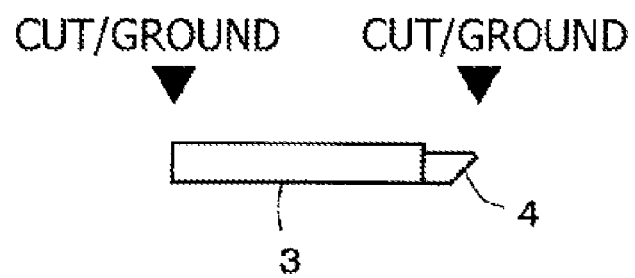
(c) 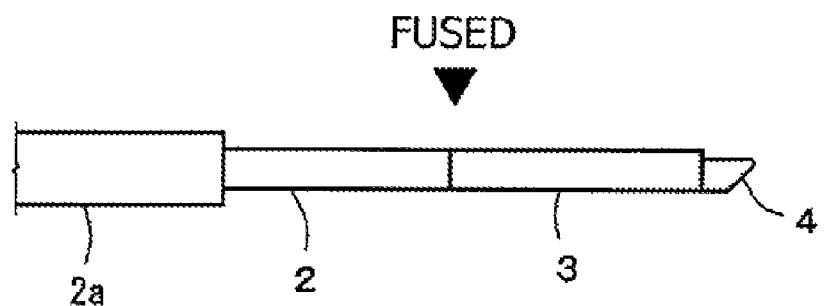

Fig. 12
(a) 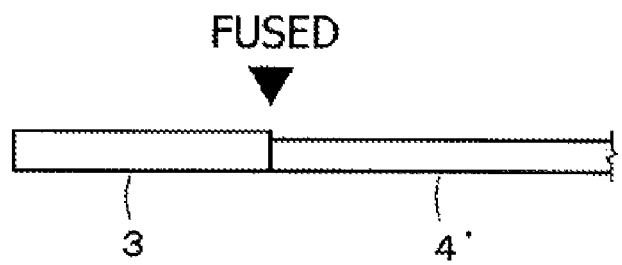
(b) 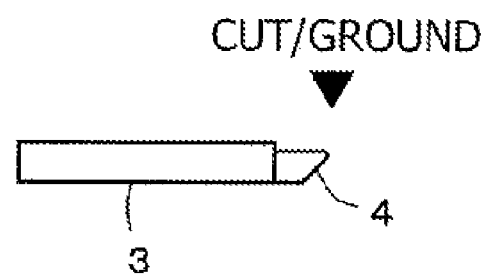
(c) 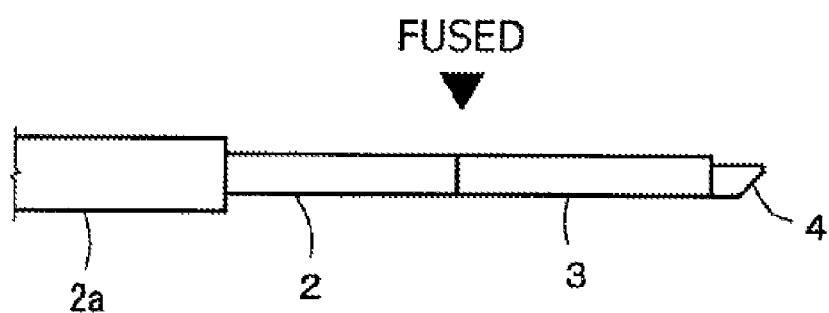

LATERAL LIGHT EMITTING DEVICE AND METHOD OF PRODUCING THE SAME

TECHNICAL FIELD

The present invention relates to a lateral light emitting device that emits light, which has propagated in an optical fiber, in a lateral direction at an angle related to the optical axis of an optical fiber, and, in particular, is suitable for use as an optical probe for OCT (Optical Coherence Tomography). The present invention also relates to a method of producing the lateral light emitting device.

BACKGROUND ART

OCT is a method of creating an optical coherence tomographic image that allows a precise tomographic image of the inside of a subject body to be obtained. OCT uses light reflected back from parts of the subject body in response to low-coherence light laterally emitted from the distal end of an optical probe inserted into an organ of the patient such as a blood vessel or the bowels. A basic technology of the OCT is disclosed in Japanese Examined Patent Application Publication No. 6-35946 (Patent Literature 1), and specific structures of the optical probes are disclosed in Japanese Unexamined Patent Application Publication No. 11-56786 (Patent Literature 2), Japanese Unexamined Patent Application Publication No. 2008-200283 (Patent Literature 3), and so forth.

FIG. 18 is a sectional explanatory view of a related-art lateral light emitting device (optical probe) described in Patent Literatures 2 and 3.

A distal end holding portion 11 is mounted at a distal end of a cylindrical shaft 10, a distal end of an optical fiber 2 that is inserted through the shaft 10 is engaged with a proximal end side of the distal end holding portion 11, and a rod lens 3, to which a prism 4 is bonded, is engaged with a distal end of the distal end holding portion 11. The entirety of the lateral light emitting device is covered with a transparent sheath 12 in order to prevent the subject body from being damaged and prevent the prism 4 and the rod lens 3 from becoming completely detached and being left inside the subject body.

CITATION LIST

Patent Literature

Patent Literature 1: Japanese Examined Patent Application Publication No. 6-35946
Patent Literature 2: Japanese Unexamined Patent Application Publication No. 11-56786
Patent Literature 3: Japanese Unexamined Patent Application Publication No. 2008-200283

In the related-art lateral light emitting device, the rod lens and the prism are bonded to each other with adhesive, and accordingly, has an adhesive layer in an optical path. Thus, there are problems such as variations in quality of a beam, and degradation of quality of a beam due to a gap between the rod lens and prism caused by, for some reason, detachment of the adhesion that bonds the rod lens and the prism together. In the worst case, a problem of the lens becoming completely detached from the prism occurs.

In addition, since the rod lens 3 and the prism 4 are very small in size, a task to bond these components together is complicated and inefficient. Since the optical fiber and the rod lens need to be engaged with the distal end holding portion 11 at the distal end of the shaft 10 with high precision, skills and time are required in assembly, thereby reducing efficiency in production.

Since the shaft 10 and sheath 12 are essential components, the outer diameter needs to be large, thereby causing a problem in that insertion into a very thin blood vessel or the like is impossible.

An object of the present invention is to solve the problems of the related-art lateral light emitting device as above and to develop a lateral light emitting device that is free from variations and degradation in beam quality and reduction in reliability caused by adhesive, can be easily produced, and has a small diameter in order to be usable for thin blood vessels and the like.

SUMMARY OF THE INVENTION

According to the present invention, a lateral light emitting device includes an optical fiber, a rod lens having a first end fused to an end surface of the optical fiber, and a prism fused to a second end of the rod lens. The prism has a basic shape including a planar light emitting surface parallel to an axis formed by cutting part of a circumference of a cylinder, and the prism includes a distal end inclined surface formed by diagonally cutting a distal end portion of the prism. Light having entered the prism from the optical fiber is reflected by the distal end inclined surface and emitted from the light emitting surface.

The optical fiber and the rod lens, and the rod lens and the prism are joined to each other by fusing. Thus, there is no adhesive layer in an optical path, and accordingly, there are no variations in beam quality, no degradation in beam quality due to detachment of the adhesion, and no complete detachment of the prism. Production can be easily performed using related-art known fiber fusing equipment.

Since the lateral light emitting device needs no shaft or sheath, the outer diameter can be made to be very small. Thus, the lateral light emitting device can be used for a very thin blood vessel and the like.

In most cases, the optical fiber is a single-mode optical fiber. However, the optical fiber may use a polarization maintaining fiber or a multi-mode fiber. In addition, the optical fiber may even use a bundle fiber for image transmission.

The rod lens needs to be formed of silica based glass in order to undergo fusing. The rod lens may use a so-called GI-type fiber, of which the core has a refractive index distribution, or a so-called GRIN lens, of which the entire section has a refractive index distribution.

The rod lens may also use a lens produced by fusing together two types of (or three or more types of) GRIN lenses each having a different numerical aperture as described in Japanese Unexamined Patent Application Publication No. 2005-115097.

The prism needs to be formed of silica based glass in order to undergo fusing. The prism has the basic shape including the planar light emitting surface parallel to the axis formed by cutting part of the circumference of the cylinder (a semi-cylindrical shape). Thus, the prism can be easily produced by drawing (formed into a fiber) a ground base material (a base material produced by grinding part of a circumference of a cylindrical base material) having a sectional shape similar to that of the prism. In addition, the prism in an elongated fiber state can be easily fused to the rod lens.

A typical inclination angle (θ in FIG. 3) of the distal end inclined surface of the prism relative to the light emitting surface is 45°. In this case, light is laterally emitted at 90° relative to the axis. By changing the inclined angle (θ) of the distal end inclined surface, the light emission angle can be changed. Coating such as mirror-coating (coated with Au or the like) or half-mirror coating (coated with a dielectric multi-layer or the like) may be applied to the distal end inclined surface according to need.

Also according to the present invention, in the lateral light emitting device described above, a most distal end portion of the prism is chamfered.

By chamfering the most distal end portion of the prism, when the lateral light emitting device is directly inserted into the subject body without being covered with a sheath, it is less likely that the subject body is damaged.

Chamfering includes a method, for example, using electric discharge or a laser in order to smooth the most distal end portion of the prism into a curved surface-like shape.

Also according to the present invention, in the lateral light emitting device described above, an outer diameter of the rod lens and a maximum diameter of the prism are less than or equal to twice a diameter of the optical fiber.

When the outer diameters of the optical fiber and the rod lens are close to each other, the axes thereof are automatically aligned with each other by self-alignment effects due to surface tension caused in fusing. This significantly reduces coupling loss between the optical fiber and the rod lens. When the outer diameter of the optical fiber is 125 μm, the outer diameter of the rod lens is suitably from 124 to 250 μm. Likewise, the maximum diameter of the prism is suitably from 124 to 250 μm. When the outer diameter of the optical fiber is 80 μm, the outer diameter of the rod lens and the maximum diameters of the prism are suitably from 79 to 160 μm.

This also meets the purpose of the device that is intended to be inserted into a thin blood vessel and the like.

Also according to the present invention, a method of producing the lateral light emitting device as described above includes the step of forming a ground base material having a planar ground surface parallel to the axis by cutting part of a circumference of a cylindrical silica glass base material, the step of forming a fiber for a prism by drawing the ground base material, the step of fusing the fiber for a prism to the rod lens or to a lens fiber, which has not been cut so as to produce the rod lens, and the step of forming the distal end inclined surface by cutting the fiber for a prism.

To produce the prism according to the present invention, the cylindrical silica glass base material is initially produced. The base material can be produced using a known method. Next, by grinding part of the circumference of the base material, the ground base material having a planar ground surface parallel to the axis is formed. This grinding can also be easily performed using typical grinding equipment. Next, the fiber for a prism is formed by drawing the ground base material. The ground base material can be drawn using drawing equipment used for optical fibers and GRIN lenses.

The method according to the present invention includes the step of fusing the fiber for a prism to the rod lens or to the lens fiber, which has not been cut so as to produce the rod lens, and the step of forming the distal end inclined surface by cutting the fiber for a prism having been fused to the rod lens or the lens fiber in order to produce the prism.

Since the elongated fiber for a prism is fused to the rod lens or the elongated lens fiber, which has not been cut so as to produce the rod lens, fusing task can be easily performed using known fiber fusing equipment. After this fusing, by cutting the fiber for a prism to a desired length, and by grinding the fiber for a prism according to need so as to form the distal end inclined surface, the prism can be produced from the fiber for a prism.

Also according to the present invention, a lateral light emitting device includes an optical fiber and a prism lens fused to an end surface of the optical fiber, in which the prism lens has a basic shape that includes a planar light emitting surface parallel to an axis formed by cutting part of a circumference of a cylinder, and the prism lens includes a distal end inclined surface formed by diagonally cutting a distal end portion or the prism lens, in which light having entered the prism lens from the optical fiber is reflected by the distal end inclined surface and emitted from the light emitting surface.

In the present invention, the optical fiber and the prism lens are joined to each other by fusing. Thus, there is no adhesive layer in an optical path, and accordingly, there are no variations in beam quality, no degradation in beam quality due to detachment of the adhesion, and no complete detachment of the prism lens. Production can be easily performed using related-art known fiber fusing equipment.

Since the lateral light emitting device needs no shaft or sheath, the outer diameter can be made to be very small. Thus, the lateral light emitting device can be used for a very thin blood vessel and the like.

In addition, since the rod lens and the prism are fused to each other so as to form the prism lens in an integral manner, the numbers of components and production steps can be decreased, thereby achieving labor saving and cost reduction.

In most cases, the optical fiber is a single-mode optical fiber. However, the optical fiber may use a polarization maintaining fiber or a multi-mode fiber. In addition, the optical fiber may even use a bundle fiber for image transmission.

The prism lens needs to be formed of silica based glass in order to undergo fusing. The prism lens may use a so-called GI-type fiber, of which the core has a refractive index distribution, or a so-called GRIN lens, of which the entire section has a refractive index distribution.

The prism lens may also use a lens produced by fusing together two types of (or three or more types of) the above-described GRIN lenses each having a different numerical aperture.

The prism lens has the basic shape that includes the planar light emitting surface parallel to the axis formed by cutting part of the circumference of the cylinder. Thus, the prism lens can be easily produced by drawing (formed into a fiber) the ground lens base material (a base material formed by grinding part of the circumference of the cylindrical lens base material) having a sectional shape similar to the prism lens. The prism lens in an elongated fiber state can also be easily fused to the optical fiber.

A typical inclination angle ($\theta$) of the distal end inclined surface of the prism lens relative to the light emitting surface is 45°. The light emission angle can be changed by changing the inclined angle ($\theta$). Coating such as mirror-coating (coated with Au or the like) or half-mirror coating (coated with a dielectric multi-layer or the like) may be applied to the distal end inclined surface according to need.

Also according to the present invention, in the lateral light emitting device described above, a most distal end portion of the prism lens is chamfered.

By chamfering the most distal end portion of the prism lens, when the lateral light emitting device is directly inserted into the subject body without being covered with a sheath, it is less likely that the subject body is damaged.

Chamfering includes a method, for example, using electric discharge or a laser in order to smooth the most distal end portion of the prism lens into a curved surface-like shape.

Also according to the present invention, in the lateral light emitting device described above, a maximum diameter of the prism lens is less than or equal to twice a diameter of the optical fiber.

When the outer diameters of the optical fiber and the rod lens are close to each other, the axes thereof are automatically aligned with each other by self-alignment effects due to surface tension caused in fusing. This significantly reduces coupling loss between the optical fiber and the prism lens. When the outer diameter of the optical fiber is 125 μm, the outer diameter of the prism lens is suitably from 124 to 250 μm. When the outer diameter of the optical fiber is 80 μm, the outer diameter of the prism lens is suitably from 79 to 160 μm. This also meets the purpose of the device that is intended to be inserted into a thin blood vessel and the like.

Also according to the present invention, a method of producing the lateral light emitting device described above includes the step of forming a ground lens base material having a planar ground surface parallel to the axis by cutting part of a circumference of a cylindrical lens base material, the step of forming a fiber for a prism lens by drawing the ground lens base material, the step of fusing the fiber for a prism lens to the optical fiber, and the step of forming the distal end inclined surface by cutting the fiber for a prism lens.

To produce the prism lens according to the present invention, the cylindrical lens base material formed of silica based glass is initially produced. The lens base material can be produced using a known method (for example, Japanese Unexamined Patent Application Publication No. 2005-115097). Next, by grinding part of the circumference of the lens base material, the ground base material having the planar ground surface parallel to the axis is formed. This grinding can also be easily performed using typical grinding equipment. Next, the fiber for a prism lens is formed by drawing the ground lens base material. The ground lens base material can be drawn using drawing equipment that is used for optical fibers and GRIN lenses.

The method of production according to the present invention includes the step of fusing the fiber for a prism lens to the optical fiber, and the step of forming the distal end inclined surface by cutting the fiber for a prism lens having been fused to the optical fiber in order to produce the prism lens.

Since the elongated fiber for a prism lens is fused to the optical fiber, a fusing task can be easily performed using known fiber fusing equipment. After this fusing, by cutting the fiber for a prism lens to a desired length, and by grinding the fiber for a prism lens according to need so as to form the distal end inclined surface, the prism lens can be produced from the fiber for a prism lens.

Advantageous Effects of Invention

In the lateral light emitting device according to the present invention, no adhesive is used. Thus, variations in beam quality due to an adhesive layer are eliminated.

Since the optical fiber and the rod lens, and the rod lens and the prism are joined to each other by fusing in an integral manner, there is no possibility of detachment of the adhesion that may degrade beam quality, or no possibility of complete detachment of the prism or the rod lens that may leave the prism or the rod lens in the subject body. Thus, the lateral light emitting device needs not be covered with the sheath.

Since the lateral light emitting device needs no shaft or sheath as required for the related art, the outer diameter of the lateral light emitting device can be made to be very small. Thus, the lateral light emitting device can be inserted into and used for a very thin blood vessel and the like.

Since the rod lens and the prism are fused to each other so as to form the prism lens in an integral manner, the numbers of components and production steps can be decreased, thereby achieving labor saving and cost reduction.

Since the prism or the prism lens has the basic shape that includes the planar light emitting surface parallel to the axis formed by cutting part of the circumference of the cylinder, an elongated fiber can be easily produced by drawing the base material having a sectional shape similar to the prism or prism lens and can undergo fusing in a fiber state. Thus, a fusing task can be easily performed.

BRIEF DESCRIPTION OF DRAWINGS

FIG. 7 is an explanatory view illustrating a production method of the lateral light emitting device according to the embodiment.

FIG. 9 is an explanatory view illustrating a production method of the lateral light emitting device according to the embodiment.

FIG. 11 is an explanatory view illustrating a production method of the lateral light emitting device according to the embodiment.

FIG. 12 is an explanatory view illustrating a production method of the lateral light emitting device according to the embodiment.

DETAILED DESCRIPTION OF THE INVENTION

Figure 1:
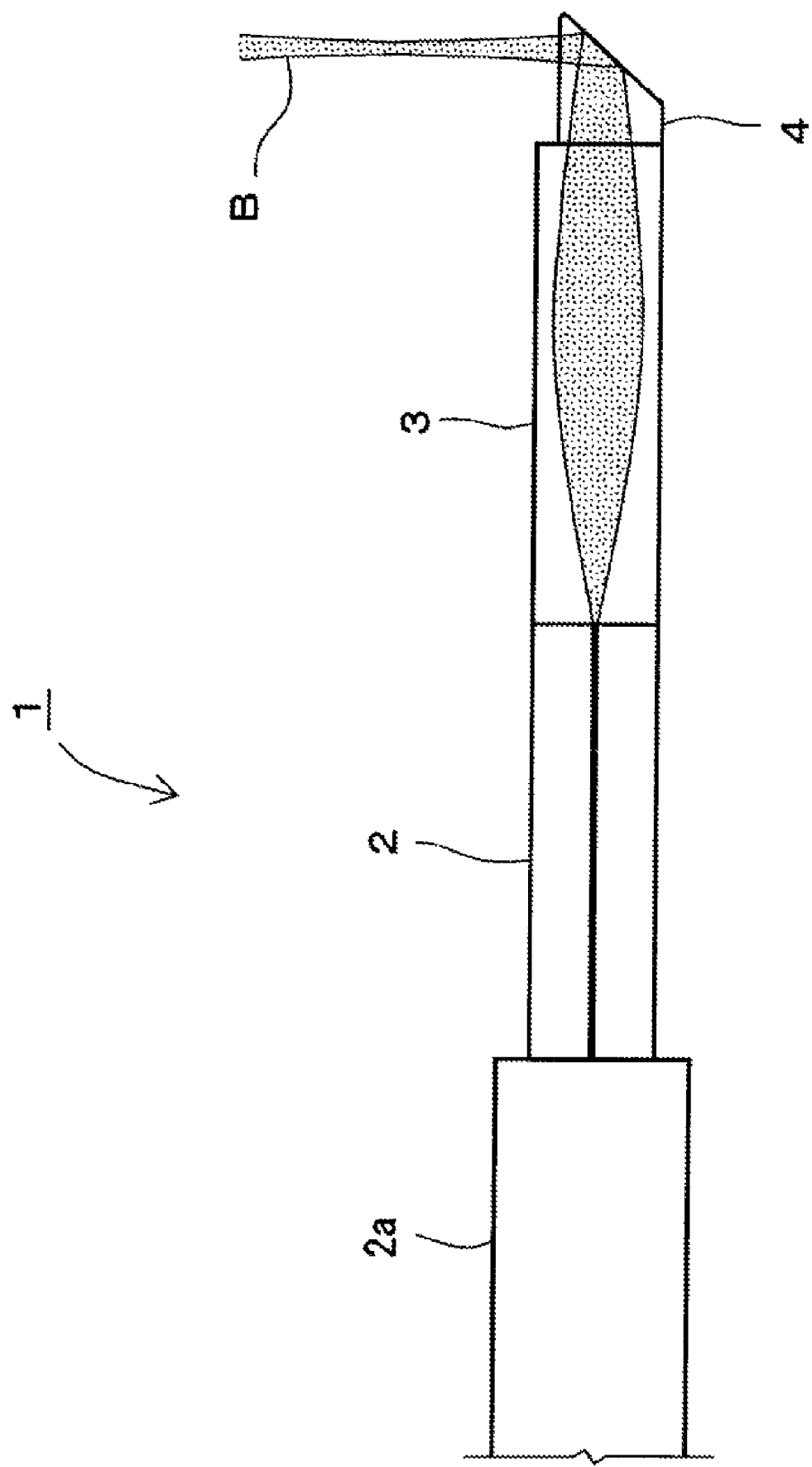
FIG. 1 is a side view of a lateral light emitting device 1 according to an embodiment.
Figure 2:
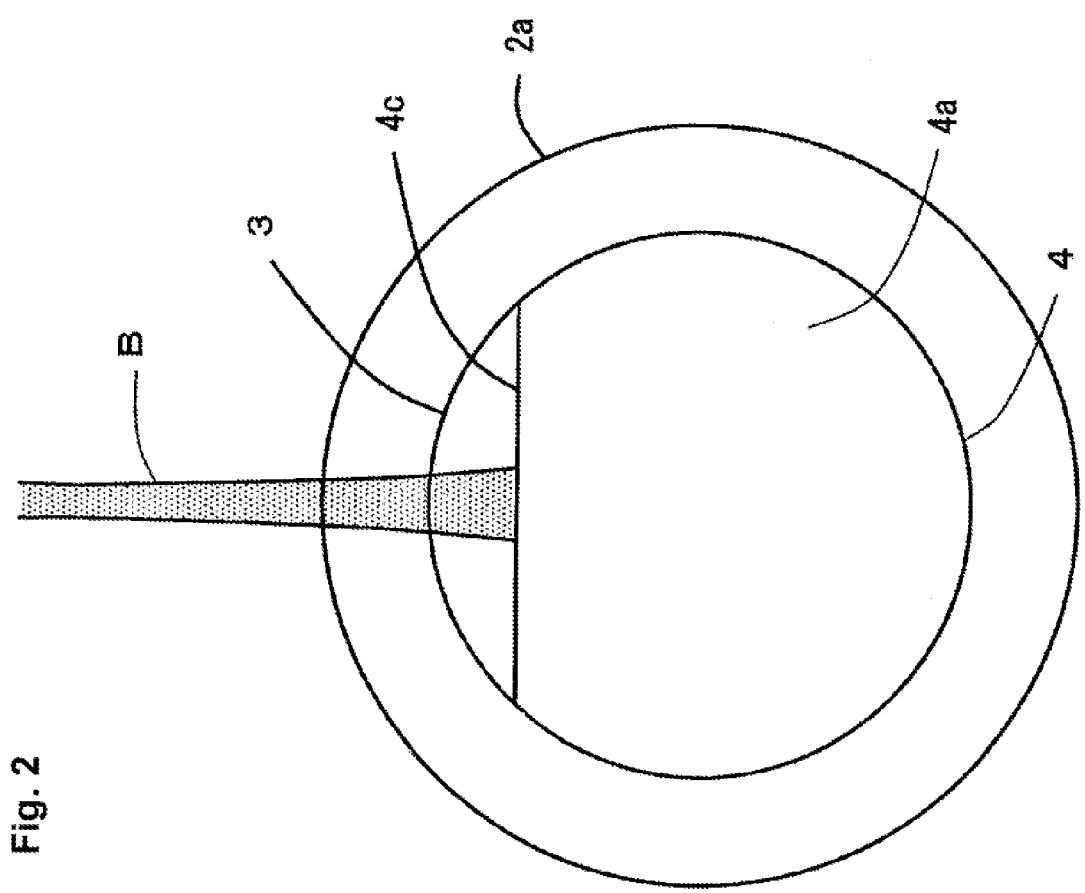
FIG. 2 is a front view of the lateral light emitting device 1.
Figure 3:
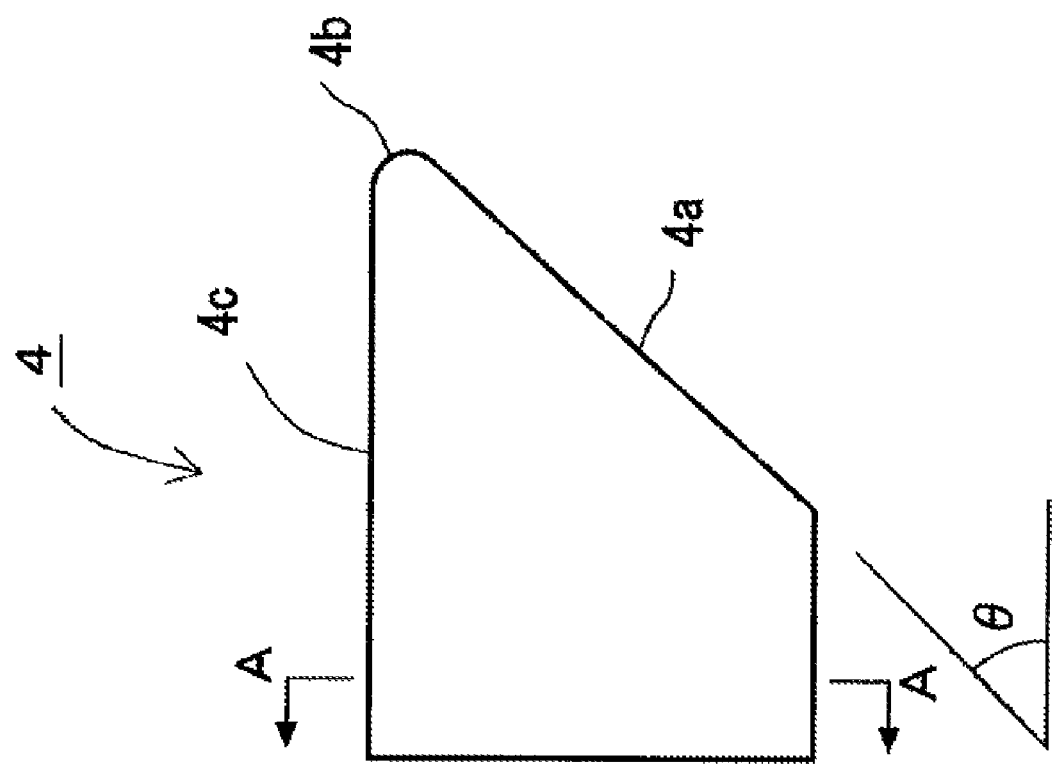
FIG. 3 is an enlarged side view of a prism 4.
Figure 4:
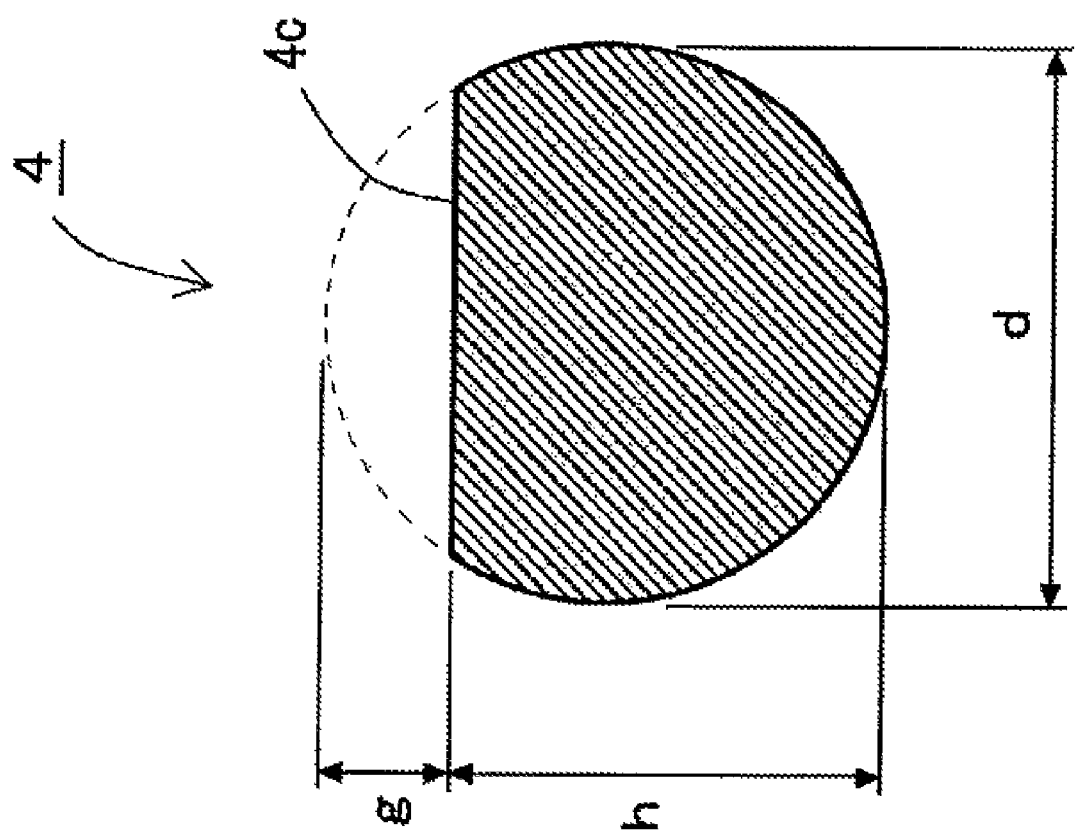
FIG. 4 is a sectional view of the prism 4 illustrated in FIG. 3 taken along line A-A.

FIGS. 1 to 4 relate to a lateral light emitting device 1 of an embodiment. FIG. 1 is a side view, FIG. 2 is a front view, FIG. 3 is an enlarged side view of a prism 4, FIG. 4 is a sectional view of the prism 4 illustrated in FIG. 3 taken along line A-A.

The lateral light emitting device 1 includes an optical fiber 2, a rod lens 3, and the prism 4.

The optical fiber 2 is a single-mode optical fiber having an outer diameter of 125 μm. A coating 2a is removed from the distal end of the optical fiber 2, and the rod lens 3 is fused to the distal end surface of the optical fiber 2.

The rod lens 3 is a GRIN lens formed of silica based glass and has an outer diameter of 125 μm. When the optical fiber 2 and the rod lens 3 are fused to each other, the axes thereof are automatically aligned with each other by self-alignment effects.

The prism 4 is formed of silica glass and has a basic shape including a planar light emitting surface 4c (the width of the light emitting surface is 74 μm) parallel to the axis formed by cutting part of a circumference of a cylinder having a diameter of d=125 μm by g=11 μm and leaving a remaining part of h=114 μm. (FIG. 4)

Figure 5:
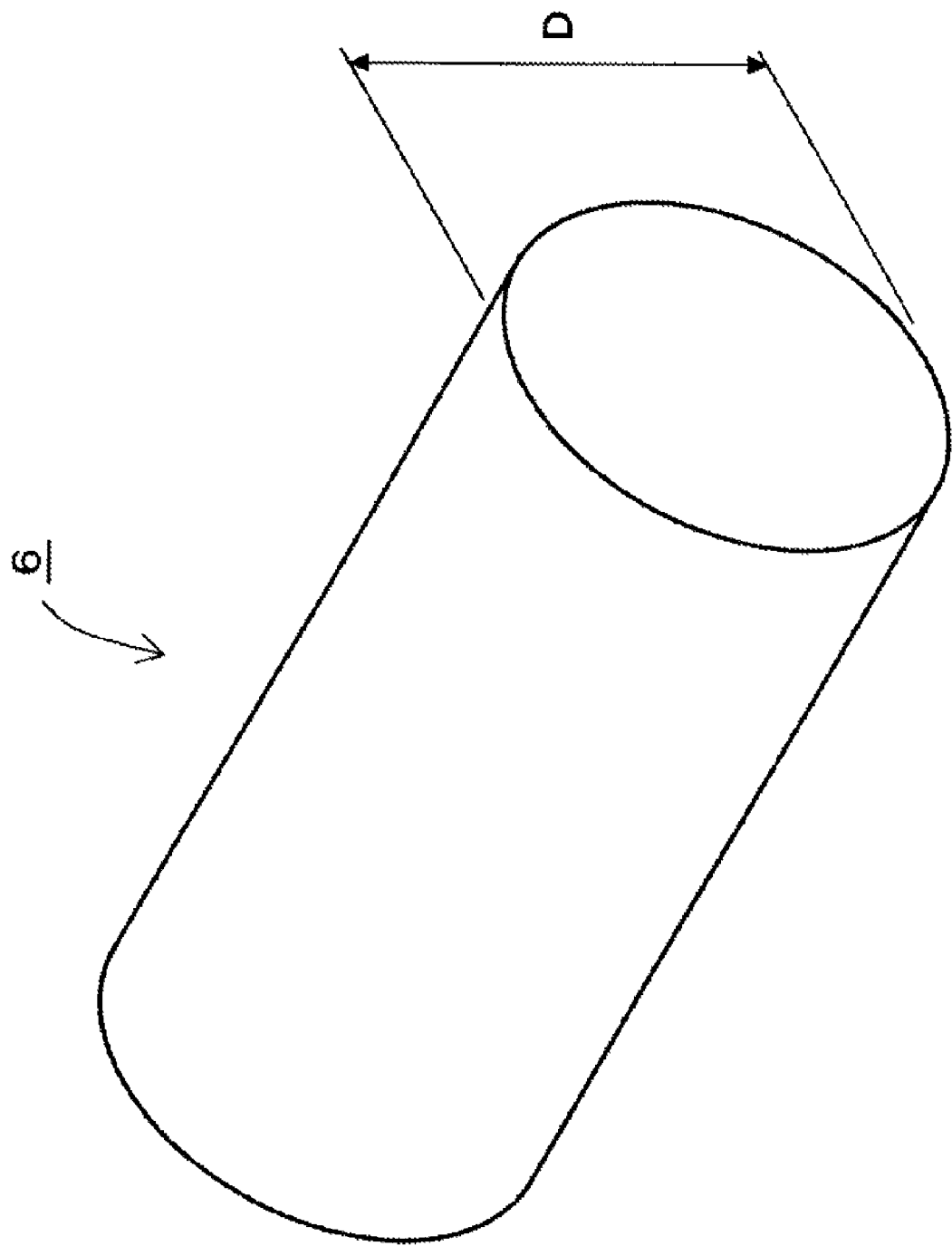
FIG. 5 is a perspective view of a base material.
Figure 6:
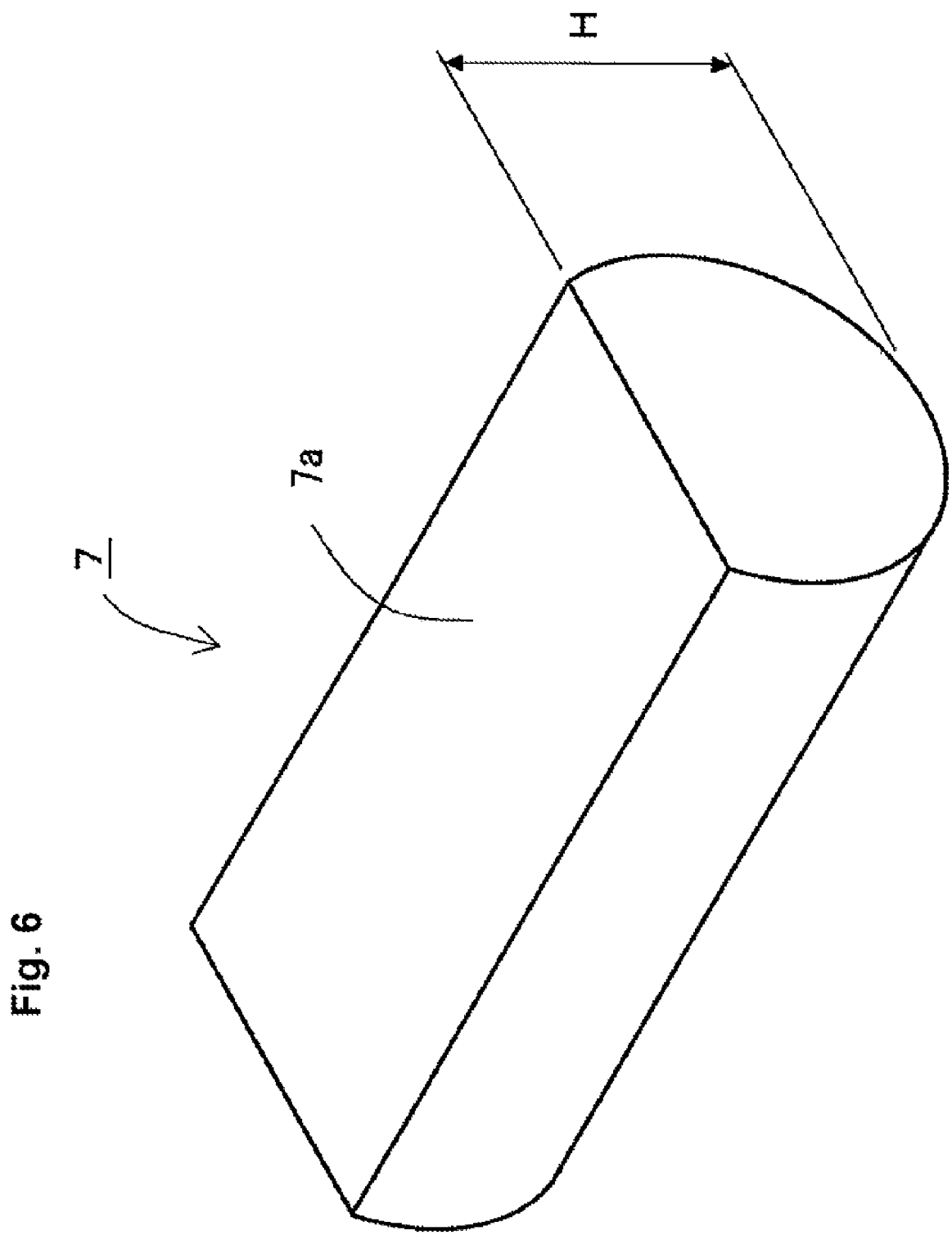
FIG. 6 is a perspective view of a ground base material.

The prism 4 is produced as follows. That is, part of a circumference of a cylindrical silica glass base material 6 illustrated in FIG. 5 having a diameter D=5.7 mm is ground by 0.7 mm so as to produce a ground base material 7 having a remaining part of H≈5 mm and the width of a ground surface 7a of about 3 mm as illustrated in FIG. 6. The resultant material is drawn at a temperature of about 1900° C. to form a fiber for a prism 4', which is cut and diagonally ground so as to form a distal end inclined surface 4a. After that, a most distal end portion 4b (i.e., an edge between the planar light emitting surface 4c and the inclined surface 4b) is chamfered using electric discharge and the distal end inclined surface 4a is Au-coated.

The ground surface 7a of the ground base material 7 is a planar surface parallel to the axis of the base material 6.

Although a typical temperature at which an optical fiber is drawn is 2000° C., it is desirable that the fiber for a prism be drawn at about 1900° C., which is a temperature lower than the typical temperature. When the drawing temperature is high, the light emitting surface 4c of the drawn fiber for a prism may be rounded. This may cause a situation in which emitted light is affected by the curvature of the light emitting surface and has an elliptic shape, thereby enlarging an illumination area, and accordingly, preventing sufficient spatial resolution from being obtained. When the drawing temperature is set to about 1900° C., the curvature of the light emitting surface 4c is very small and the light emitting surface 4c becomes a substantially planar surface, which causes no problem in practical use.

Light emitted from the optical fiber 2 enters the rod lens 3 while diverging, advances in the rod lens 3 while converging, enters the prism 4, is reflected by the distal end inclined surface 4a, and is emitted from the light emitting surface 4c.

The lateral light emitting device 1 can be easily produced using methods illustrated in FIGS. 7 to 12.

Referring to FIG. 7, (a) illustrates a state in which a lens fiber 3' is fused to one end of the optical fiber 2, (b) illustrates a state in which the lens fiber 3' is cut to a specified length (after the cutting, the cut surface may be ground according to need) so as to produce the rod lens 3, (c) illustrates a state in which the fiber for a prism 4' is fused to an end surface of the rod lens 3, and (d) illustrates a state in which the fiber for a prism 4' is cut and ground so as to form the distal end inclined surface, and then the most distal end portion 4b is chamfered and the distal end inclined surface 4a is Au-coated so as to produce the prism 4.

The lens fiber 3' is a fiber-like material that is formed by drawing a GRIN lens base material.

Figure 8:
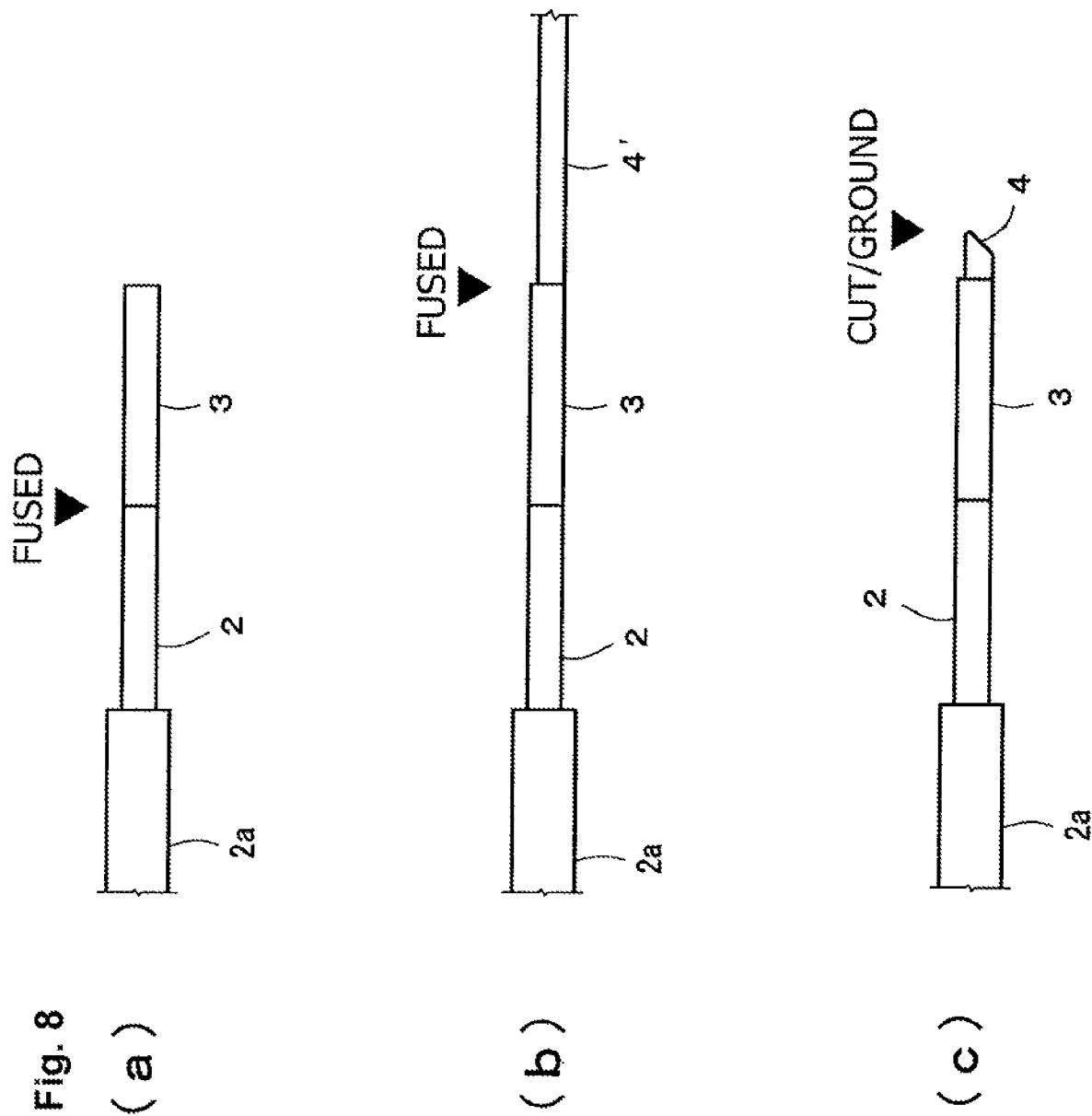
FIG. 8 is an explanatory view illustrating a production method of the lateral light emitting device according to the embodiment.

Referring to FIG. 8, (a) illustrates a state in which the rod lens 3, which has been produced in advance, is fused to one end of the optical fiber 2, (b) illustrates a state in which the fiber for a prism 4' is fused to the end surface of the rod lens 3, and (c) illustrates a state in which the fiber for a prism 4' is cut and ground so as to form the distal end inclined surface. Then, the most distal end portion 4b is chamfered and the distal end inclined surface 4a is Au-coated so as to produce the prism 4.

Referring to FIG. 9, (a) illustrates a state in which the fiber for a prism 4' is fused to one end of the lens fiber 3', (b) illustrates a state in which the lens fiber 3' is cut to a specified length (after the cutting, the cut surface may be ground according to need) so as to produce the rod lens 3, (c) illustrates a state in which the end surface of the rod lens 3 is fused to one end of the optical fiber 2, and (d) illustrates a state in which the fiber for a prism 4' is cut and ground so as to form the distal end inclined surface, and then the most distal end portion 4b is chamfered and the distal end inclined surface 4a is Au-coated so as to produce the prism 4.

Figure 10:
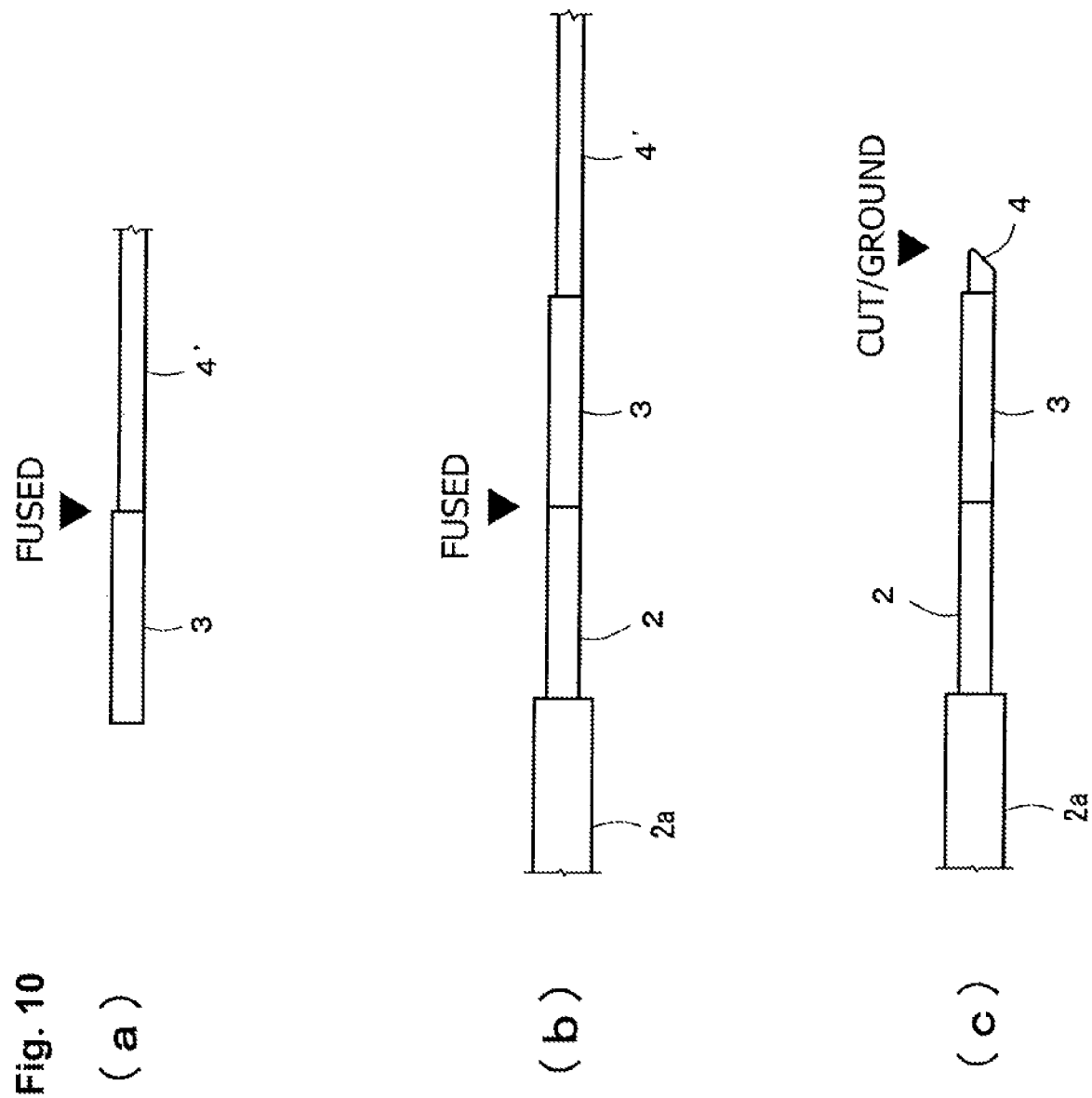
FIG. 10 is an explanatory view illustrating a production method of the lateral light emitting device according to the embodiment.

Referring to FIG. 10, (a) illustrates a state in which the fiber for a prism 4' is fused to one end of the rod lens 3 that has been produced in advance, (b) illustrates a state in which the end surface of the rod lens 3 is fused to one end of the optical fiber 2, and (c) illustrates a state in which the fiber for a prism 4' is cut and ground so as to form the distal end inclined surface. Then, the most distal end portion 4b is chamfered and the distal end inclined surface 4a is Au-coated so as to produce the prism 4.

Referring to FIG. 11, (a) illustrates a state in which the fiber for a prism 4' is fused to one end of the lens fiber 3', (b) illustrates a state in which the lens fiber 3' is cut to a specified length (after the cutting, the cut surface may be ground according to need) so as to produce the rod lens 3, the fiber for a prism is cut and ground so as to form the distal end inclined surface, and then the most distal end portion 4b is chamfered and the distal end inclined surface 4a is Au-coated so as to produce the prism 4, thereby producing a rod lens with a prism, and (c) illustrates a state in which the rod lens with a prism is fused to the optical fiber 2.

Referring to FIG. 12, (a) illustrates a state in which the fiber for a prism 4' is fused to one end of the rod lens 3 that has been produced in advance, (b) illustrates a state in which the fiber for a prism is cut and ground so as to form the distal end inclined surface, and then the most distal end portion 4b is chamfered and the distal end inclined surface 4a is Au-coated so as to produce the prism 4, thereby producing the rod lens with a prism, and (c) illustrates a state in which the rod lens with a prism is fused to one end of the optical fiber 2.

Figure 13:
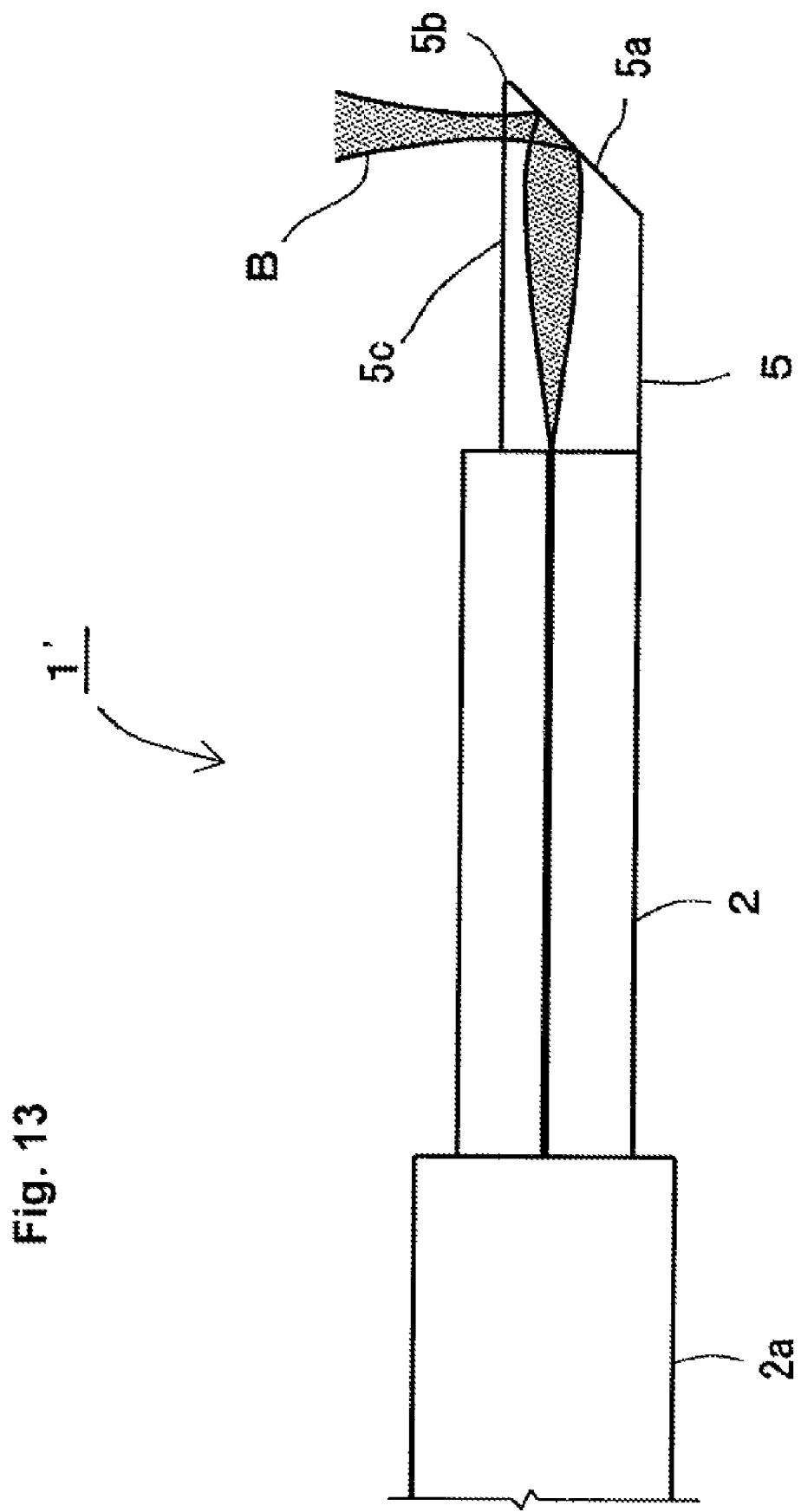
FIG. 13 is a side view of a lateral light emitting device 1' according to an embodiment.

In a lateral light emitting device 1' illustrated in FIG. 13, a prism lens 5 is fused to an end surface of the optical fiber 2. The optical fiber 2 is a single-mode optical fiber having the outer diameter of 125 μm. The coating 2a is removed at the distal end of the optical fiber 2.

Figure 14:
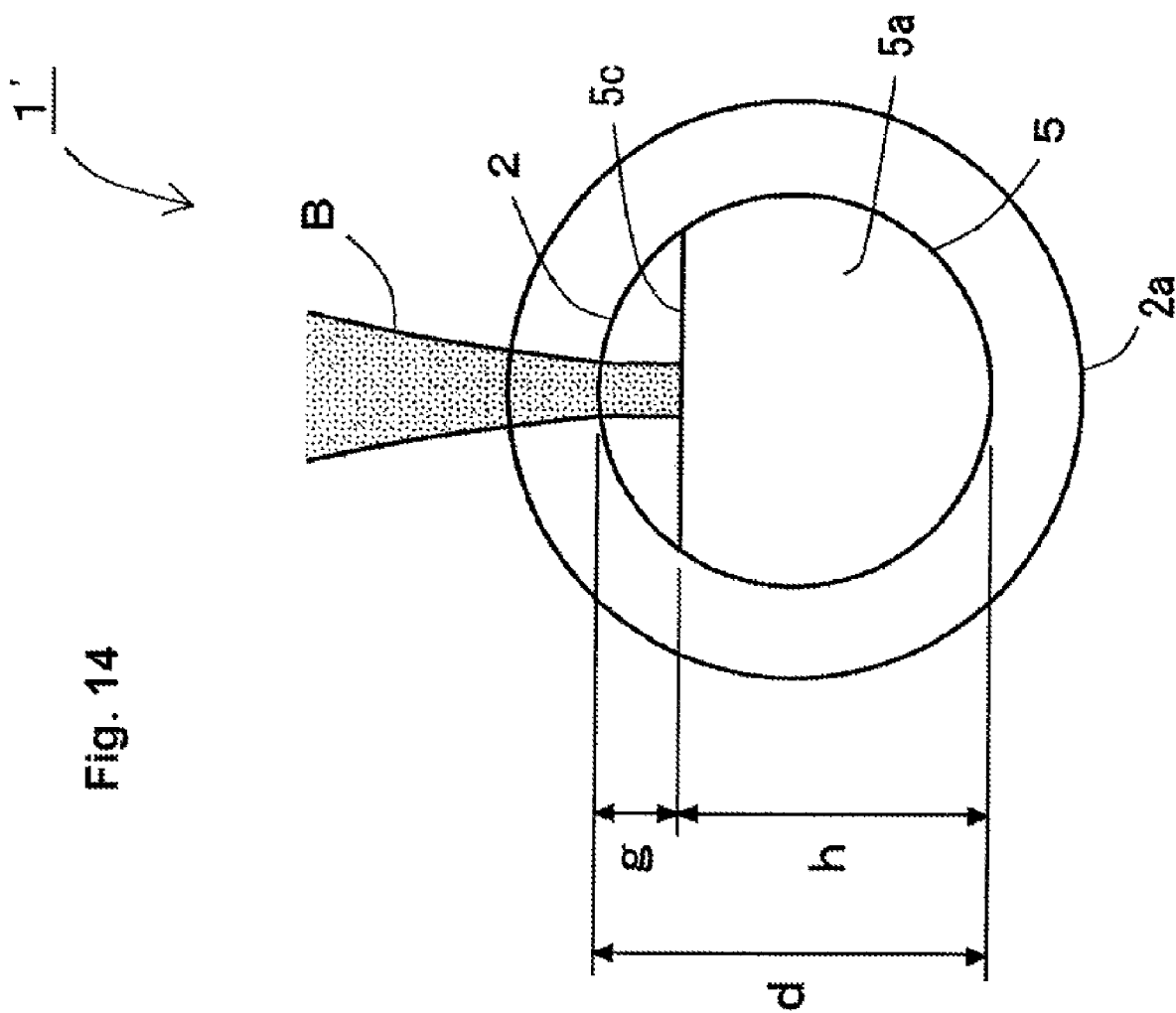
FIG. 14 is a front view of the lateral light emitting device 1'.

The prism lens 5 is a GRIN lens having a numerical aperture of 0.17, and has a basic shape including a planar light emitting surface 5c (the width of the light emitting surface is 74 μm) parallel to the axis formed by cutting part of a circumference of a cylinder having a diameter of d=125 μm by g=11 μm and leaving a remaining part of h=114 μm. (FIG. 14) The distal end portion of the prism lens 5 is diagonally cut so as to form a distal end inclined surface 5a.

The entire length of the prism lens 5 is 300 μm.

Figure 15:
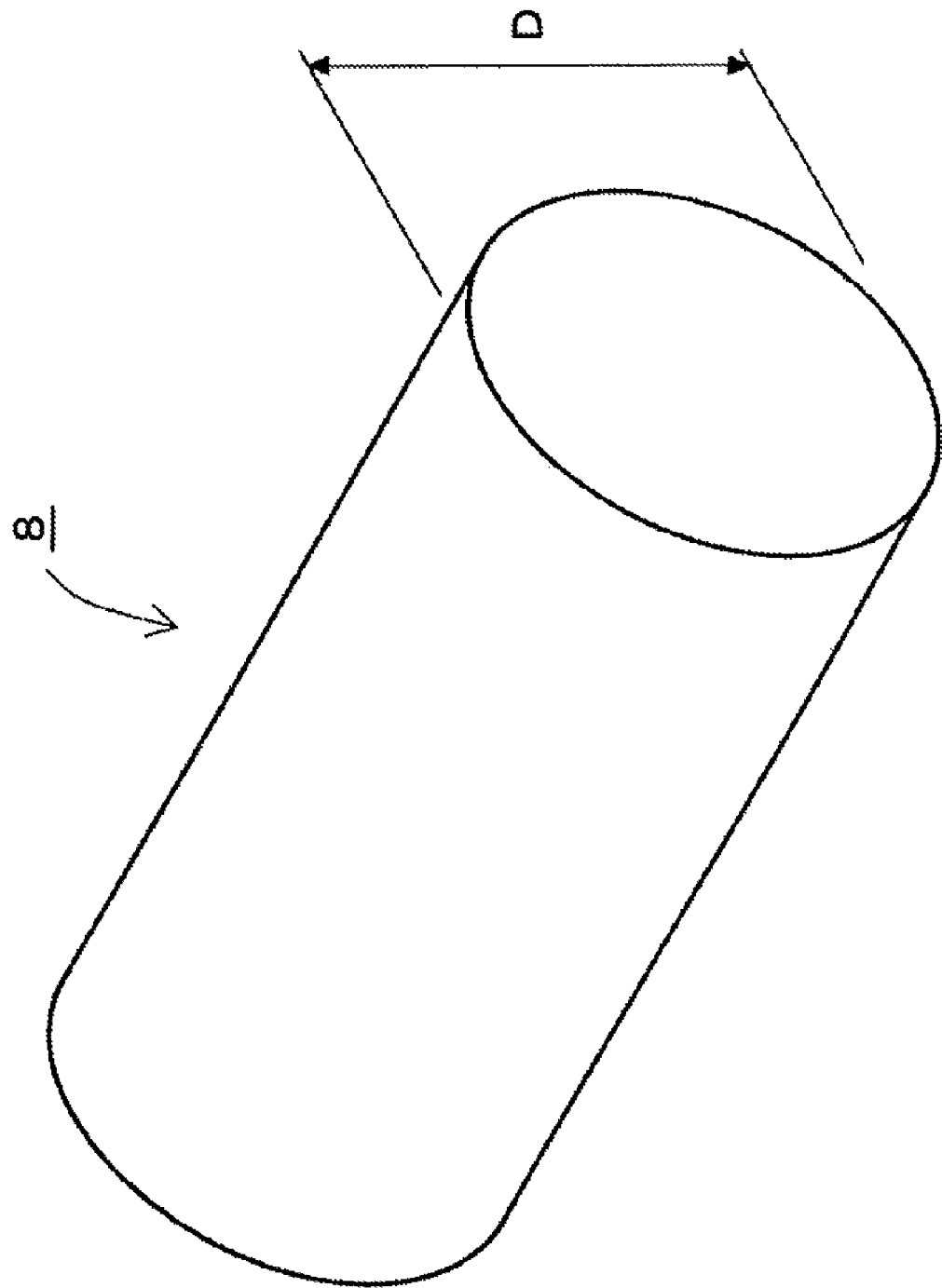
FIG. 15 is a perspective view of a lens base material 8.
Figure 16:
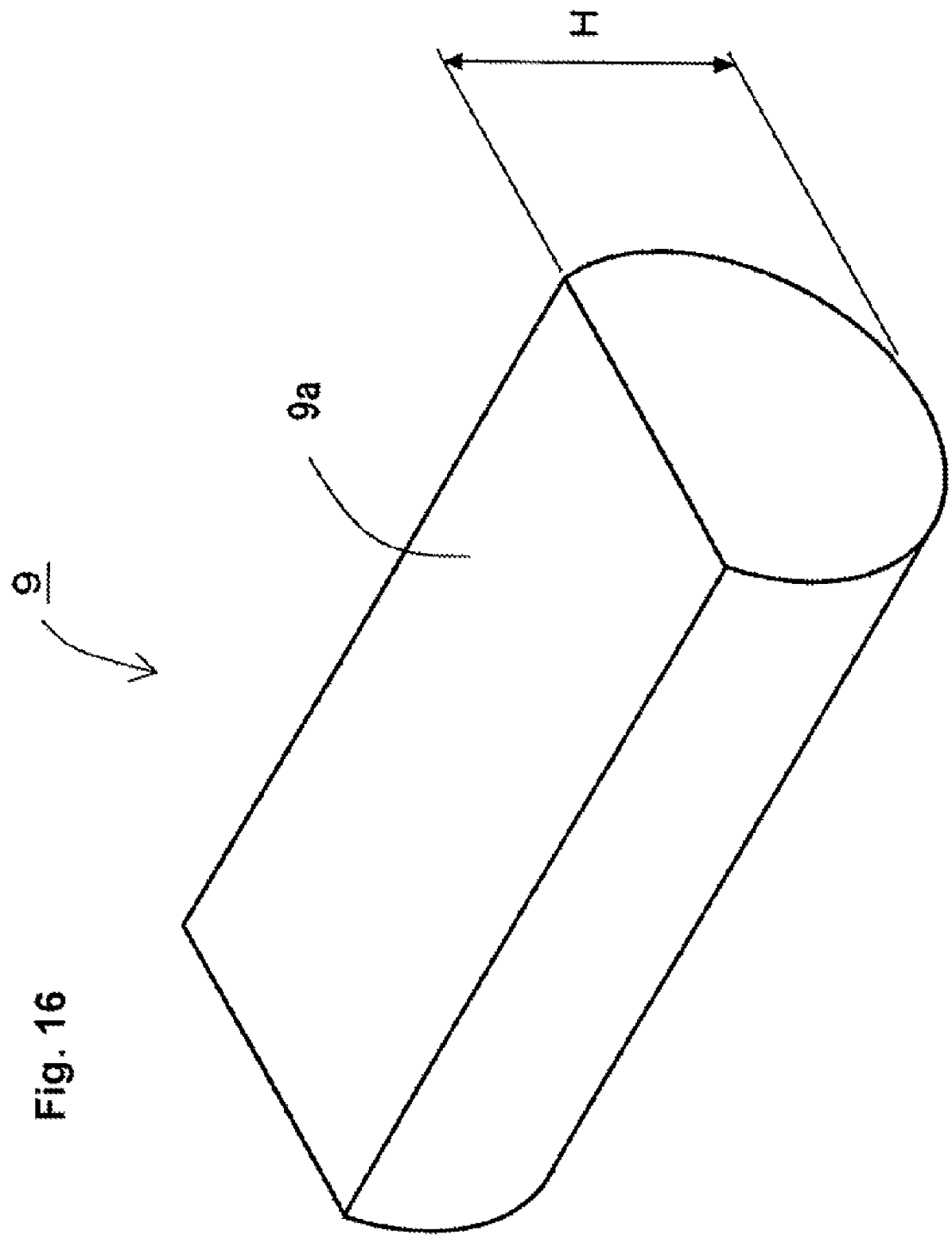
FIG. 16 is a perspective view of a ground lens base material 9.

The prism lens 5 is produced as follows. That is, part of the circumference of a cylindrical GRIN lens base material 8 illustrated in FIG. 15 having a diameter of D=5.0 mm is ground by about 0.5 mm so as to produce a ground lens base material 9 having a remaining part of H≈4.5 mm and the width of a ground surface 9a of about 3 mm as illustrated in FIG. 16. The resultant material is drawn at a temperature of about 1800° C. to form a fiber for a prism lens 5', which is cut and diagonally ground so as to form the distal end inclined surface 5a. After that, a most distal end portion 5b is chamfered using electric discharge and the distal end inclined surface 5a is Au-coated.

The ground surface 9a of the ground lens base material 9 is a planar surface parallel to the axis of the lens base material 8.

Although a typical temperature at which a GRIN lens fiber having a numerical aperture of 0.17 is drawn is 1900° C., it is desirable that the fiber for a prism lens be drawn at about 1800° C., which is a temperature lower than the typical temperature. When the drawing temperature is high, the light emitting surface 5c of the drawn fiber for a prism lens may be rounded. This may cause a situation in which emitted light is affected by the curvature of the light emitting surface and has an elliptic shape, thereby enlarging an illumination area, and accordingly, preventing sufficient spatial resolution from being obtained. When the drawing temperature is set to about 1800° C., the curvature of the light emitting surface 5c is very small and the light emitting surface 5c becomes a substantially planar surface, which causes no problem in practical use.

Light emitted from the optical fiber 2 enters the prism lens 5 while diverging, advances in the prism lens 5 while converging, is reflected by the distal end inclined surface 5a, and is emitted from the light emitting surface 5c.

Figure 17:
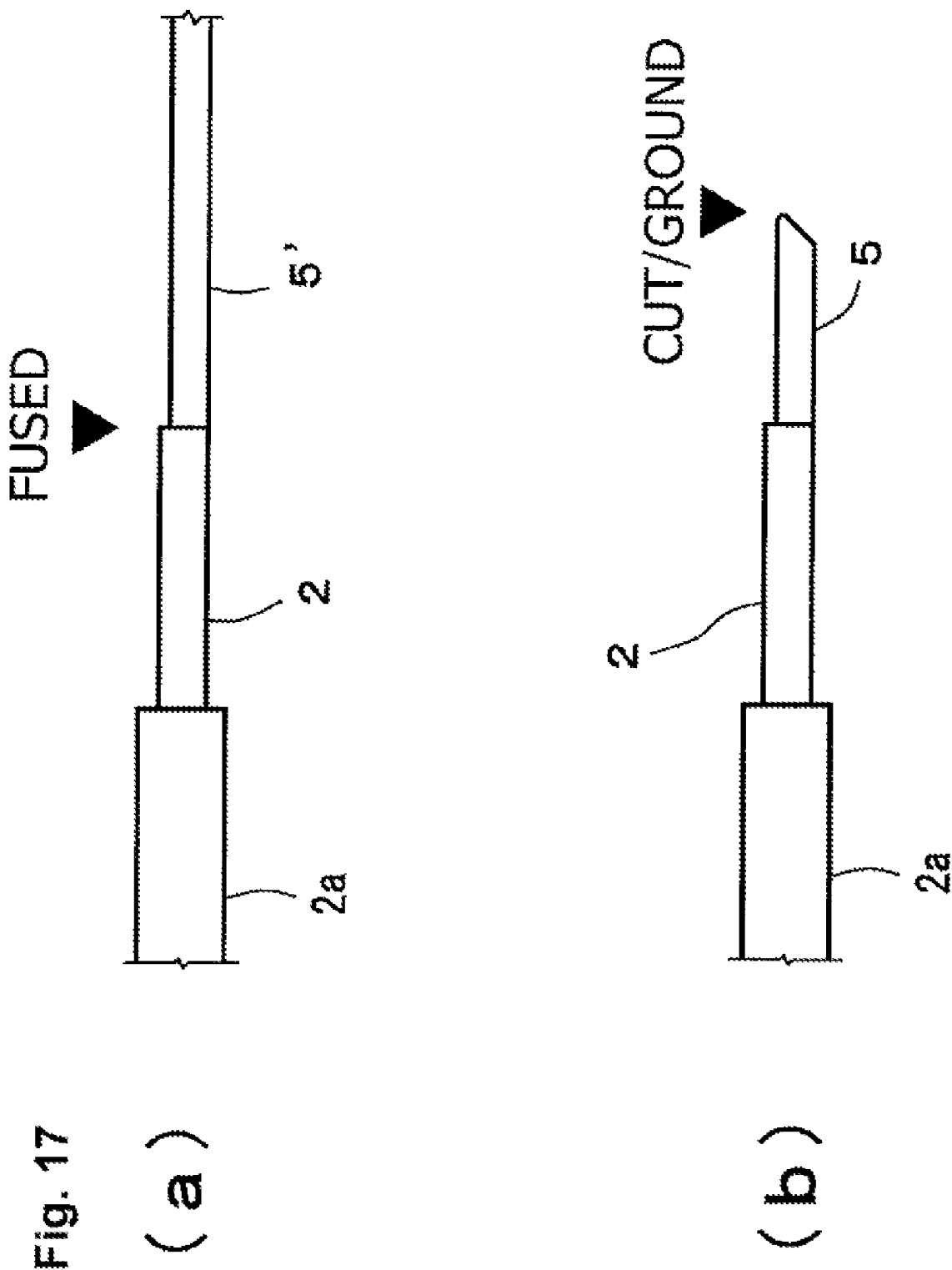
FIG. 17 is an explanatory view illustrating a production method of the lateral light emitting device according to the embodiment.
Figure 18:
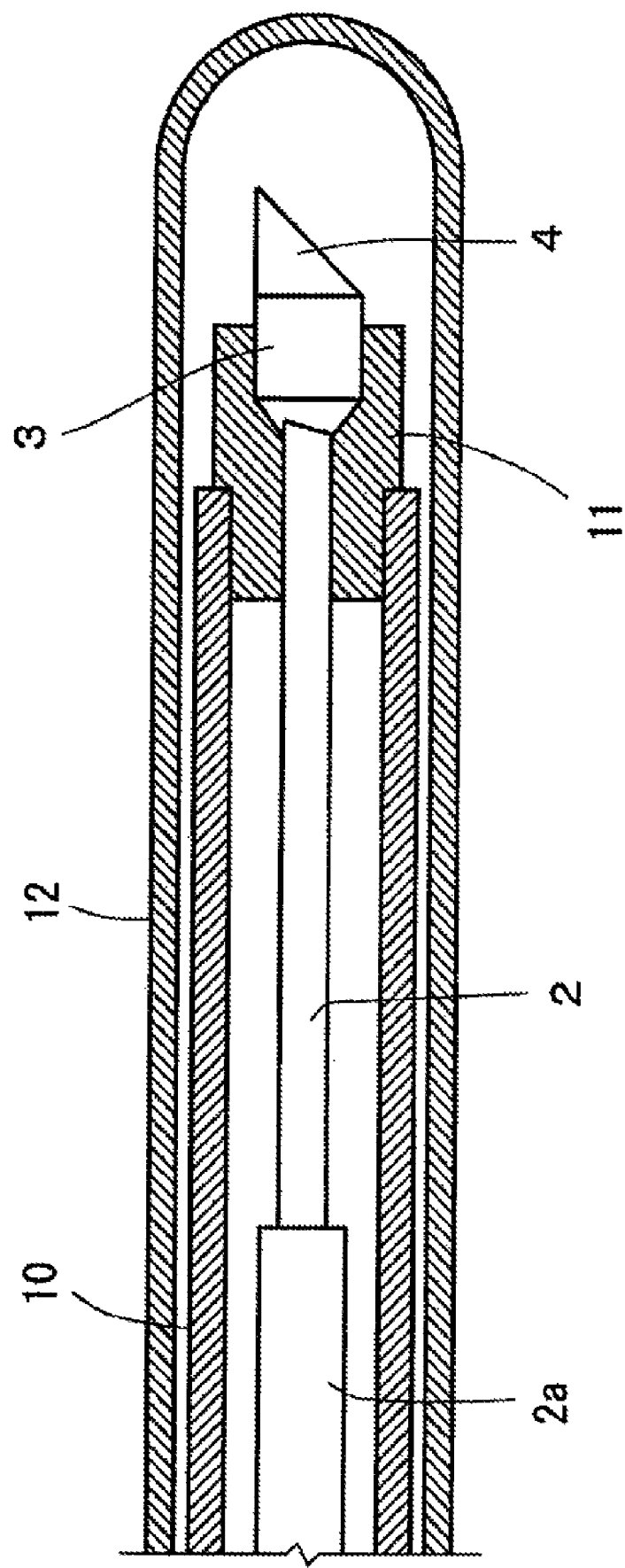
FIG. 18 is a sectional explanatory view of a related-art lateral light emitting device.

The lateral light emitting device 1' is easily produced by a production method illustrated in FIG. 17.

Referring to FIG. 17, (a) illustrates a state in which the fiber for a prism lens 5' is fused to a distal end of the optical fiber 2, (b) illustrates a state in which the fiber for a prism lens 5' is cut and ground so as to form the distal end inclined surface, and then the most distal end portion 5b is chamfered and the distal end inclined surface 5a is Au-coated so as to produce the prism lens 5.

The lateral light emitting device 1' having a diameter the same as that of the optical fiber is very thin and suitably used for very thin blood vessels and the like.

According to the present invention, the distal end inclined surface of the prism or the prism lens can be also formed by cutting the fiber for a prism or the fiber for a prism lens using a laser so as to form the inclined surface other than cutting and grinding.

INDUSTRIAL APPLICABILITY

The lateral light emitting device according to the present invention can be used as an optical probe for OCT, and in addition, used as a fiber-optic module for optical communication, for example, for combining a laser diode and a single-mode fiber, an optical probe for distance and displacement sensors, an optical probe for an endoscope, and so forth.

REFERENCE SIGNS LIST 1 lateral light emitting device
2 optical fiber
2a coating
3 rod lens
3' lens fiber
4 prism
4a distal end inclined surface
4b most distal end portion
4c light emitting surface
4' fiber for a prism
5 prism lens
5a distal end inclined surface
5b most distal end portion
5c light emitting surface
5' fiber for a prism lens
6 base material
7 ground base material
7a ground surface
8 lens base material
9 ground lens base material
9a ground surface
10 shaft
11 distal end holding portion
12 sheath
B emitted light

The invention claimed is:

1. A lateral light emitting device comprising:
   an optical fiber; and
   a prism GRIN lens fused to an end surface of said optical fiber, said prism GRIN lens having:
      a planar light emitting surface parallel to a longitudinal axis thereof, said planar light emitting surface being formed by cutting a circumference of a cylinder;
      an inclined surface at a distal end of said prism GRIN lens, said inclined surface being formed by diagonally cutting a distal end portion of said prism GRIN lens so that light having entered said prism GRIN, lens from said optical fiber is reflected by said inclined surface and emitted from said light emitting surface.

2. The lateral light emitting device of claim 1, wherein a furthermost distal end portion of said prism GRIN lens is chamfered.

3. The lateral light emitting device of claim 2, wherein said furthermost distal end portion is an edge between said light emitting surface and said inclined surface at said distal end.

4. The lateral light emitting device of claim 2, wherein a maximum diameter of said prism GRIN lens is less than or equal to twice a diameter of said optical fiber.

5. A method of producing the lateral light emitting device of claim 2, comprising:
   forming a ground GRIN lens base material having a planar ground surface parallel to a longitudinal axis of said ground lens base material by cutting a circumference of a cylindrical GRIN lens base material;
   forming a fiber for said prism GRIN lens by drawing said ground GRIN lens base material;
   fusing said fiber to said optical fiber; and
   forming said inclined surface at said distal end by cutting said fiber to form said prism GRIN lens.

6. The method of claim 5, wherein said forming said fiber for said prism GRIN lens by drawing said ground GRIN lens base material comprises drawing said ground GRIN lens base material at a temperature of about 1800° C.

7. The lateral light emitting device of claim 1, wherein a maximum diameter of said prism GRIN lens is less than or equal to twice a diameter of said optical fiber.

8. A method of producing the lateral light emitting device of claim 7, comprising:
   forming a ground GRIN lens base material having a planar ground surface parallel to a longitudinal axis of said ground GRIN lens base material by cutting a circumference of a cylindrical GRIN lens base material;
   forming a fiber for said prism GRIN lens by drawing said ground GRIN lens base material;
   fusing said fiber to said optical fiber; and
   forming said inclined surface at said distal end by cutting said fiber to form said prism GRIN lens.

9. The method of claim 8, wherein said forming said fiber for said prism GRIN lens by drawing said ground lens base material comprises drawing said ground lens base material at a temperature of about 1800° C.

10. A method of producing the lateral light emitting device of claim 1, comprising:

forming a ground GRIN lens base material having a planar ground surface parallel to a longitudinal axis of said ground lens base material by cutting a circumference of a cylindrical GRIN lens base material;

forming a fiber for said prism GRIN lens by drawing said ground GRIN lens base material;

fusing said fiber to said optical fiber; and forming said inclined surface at said distal end by cutting said fiber to form said prism GRIN lens.

* * * * *